(12) United States Patent
Eckburg et al.

(10) Patent No.: US 8,921,293 B1
(45) Date of Patent: Dec. 30, 2014

(54) SKIN SCRUBBING SYSTEMS

(71) Applicants: Aaron L Eckburg, Fountain Hills, AZ (US); Elizabeth L Eckburg, Fountain Hills, AZ (US)

(72) Inventors: Aaron L Eckburg, Fountain Hills, AZ (US); Elizabeth L Eckburg, Fountain Hills, AZ (US)

( * ) Notice: Subject to any disclaimer, the term of this patent is extended or adjusted under 35 U.S.C. 154(b) by 0 days.

(21) Appl. No.: 13/678,287

(22) Filed: Nov. 15, 2012

(51) Int. Cl.
*A61K 8/97* (2006.01)
*A61K 8/60* (2006.01)
*A61K 8/25* (2006.01)
*A61Q 19/10* (2006.01)

(52) U.S. Cl.
CPC ... *A61K 8/60* (2013.01); *A61K 8/97* (2013.01); *A61K 8/25* (2013.01); *A61Q 19/10* (2013.01)

USPC .......................................... 510/130; 510/139

(58) Field of Classification Search
CPC ............ A61K 8/35; A61K 8/97; A61K 36/77
See application file for complete search history.

(56) References Cited

U.S. PATENT DOCUMENTS

2007/0196324 A1* 8/2007 Keefe et al. ................ 424/78.03

* cited by examiner

*Primary Examiner* — Necholus Ogden, Jr.
(74) *Attorney, Agent, or Firm* — Andrew P. Lahser

(57) ABSTRACT

Disclosed is a method to produce, store or ship a dry scrub for the skin of a person. The dry scrub combines dry granules of sea salt, unrefined sugar, and bamboo leaf extract into a mixture. The dry scrub combines with a liquid carrier to form a skin scrub immediately prior to application to the skin.

19 Claims, 2 Drawing Sheets

SKIN SCRUBBING SYSTEMS

BACKGROUND

Applicants are a good-looking, married couple who enjoy cleansed, exfoliated, healthy skin and do not enjoy long stretches between facial scrubs.

OBJECTS AND FEATURES

A primary object and feature of the present invention is to provide a method for packaging and for storing skin scrubs to provide increased shelf life.

It is a further object and feature of the present invention to provide a method for producing a skin scrub compatible with many different skin types.

Another object and feature of the present invention is to provide a method for packaging, storing, shipping, or using a skin scrub without chemical preservatives.

Yet another object and feature of the present invention is to provide a wide variety of health benefits related to skin scrubs.

A further primary object and feature of the present invention is to provide such a method that is safe, efficient, trustworthy, inexpensive and handy. Other objects and features of the present invention will become apparent with reference to the following descriptions.

CROSS REFERENCE TO RELATED APPLICATIONS

Not applicable.

SUMMARY

Disclosed is a method to produce, store or ship a dry scrub for the skin of a person. The dry scrub combines dry granules of sea salt, unrefined sugar, and bamboo leaf extract into a mixture. The dry scrub combines with a liquid carrier to form a skin scrub immediately prior to application to the skin.

DETAILED DESCRIPTION

The present Skin Scrubbing Method will now be discussed in detail with regard to the attached drawing figures, which were briefly described above. In the following description, numerous specific details are set forth illustrating the Applicants' best mode for practicing the Skin Scrubbing Method and enabling one of ordinary skill in the art to use the Skin Scrubbing Method. It will be obvious, however, to one skilled in the art that the present Skin Scrubbing Method may be practiced without many of these specific details. In other instances, well-known manufacturing methods, cosmetic engineering considerations, preferences and best practices for skin health care, and other details have not been described in particular detail in order to avoid unnecessarily obscuring this disclosure.

At the time of writing this patent application, commercially available facial scrubs are available in liquid form. To maintain shelf life and to provide stabilization, these liquid facial scrubs contain chemical preservatives. As a result, the chemical preservatives are delivered to the skin along with the facial scrub. These facial scrubs will commonly be marked "all-natural", even though they contain chemically stabilizing preservatives. Placing chemically stabilizing preservatives on the skin may be detrimental to health.

The present invention provides a method for producing, shipping, storing and applying a dry scrub. The dry scrub may be partially dissolved in a liquid immediately prior to application to the skin by the consumer. This overcomes at least three problems with existing liquid skin scrubs. First, the dry scrub is inherently stable and may possess an indefinite shelf life. Second, the dry scrub may be combined with the most appropriate liquid for the consumers' skin type, broadening the appeal of the dry scrub. Third, the dry scrub avoids delivering potentially unhealthy chemicals, stabilizers or preservatives to the skin of the consumer. Other advantages may become apparent upon reading this description.

Figure 1:
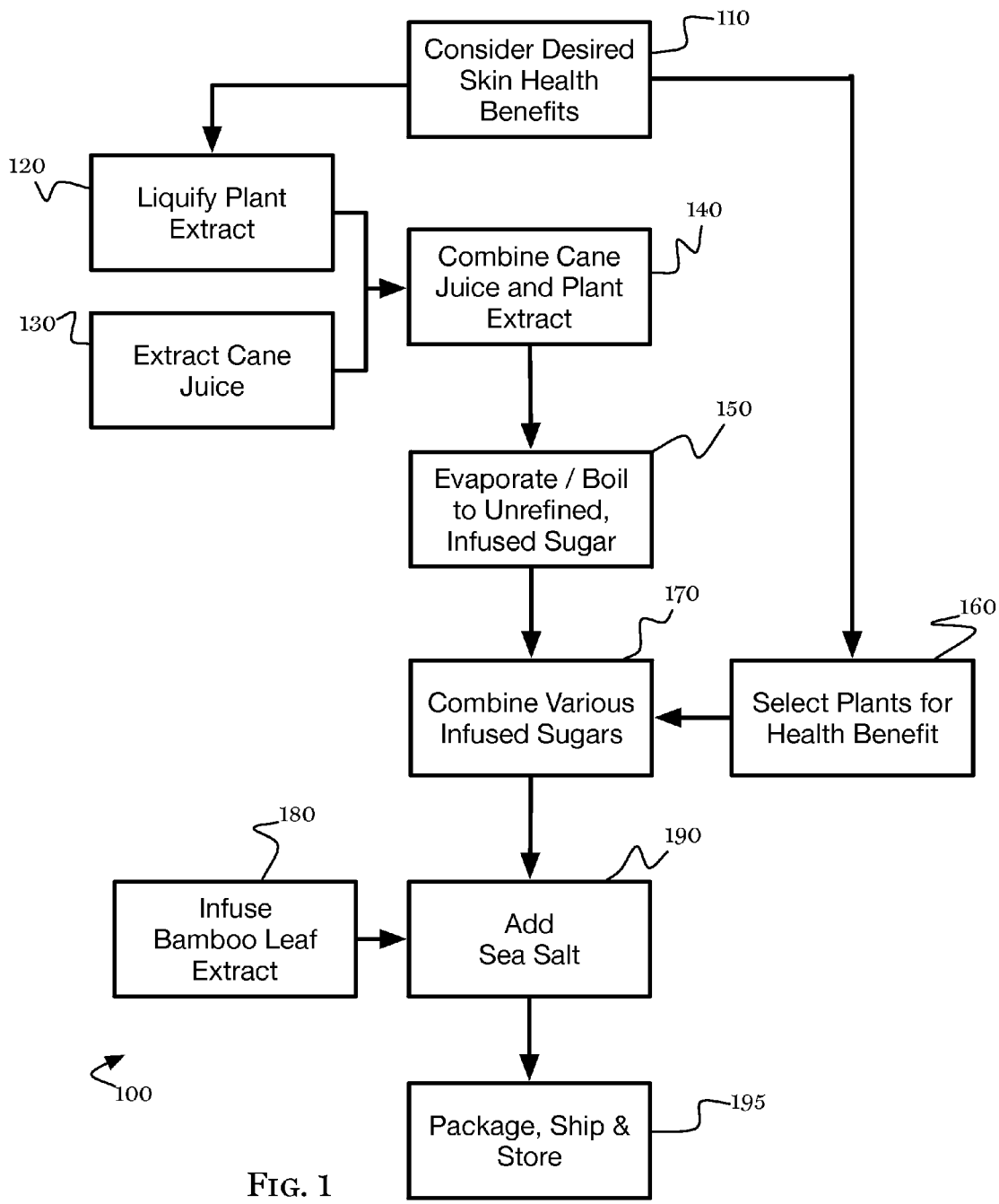
FIG. 1 shows a diagrammatic view that illustrates a method of producing a dry-granular mixture suitable for packaging, shipping, and storing for later use as a skin scrub.

FIG. 1 shows a diagrammatic view that illustrates method 100 of producing a dry-granular mixture (dry scrub) suitable for packaging, shipping, and storing for later use as a skin scrub. Step 110 allows for design of a skin scrub by considering the desired health benefits. For example, during this step the developer or manufacturer of the skin scrub could decide that a skin scrub was needed to help reduce the chance of skin cancer, to help treat skin conditions related to acne, etc. (See step 160 below for a description of combinations of plant extracts to achieve desired health benefits.)

Step 120 provides for extraction or liquefaction of the plants. Step 130 provides for extraction of cane juice from the cane plant (i.e. cane sugar plant). Step 140 combines the plant extract and the cane extract. Step 150 completes the process of making unrefined cane sugar that contains plant extract. Unrefined cane sugar may be organic cane sugar, and, may be commercially known as "raw sugar" or "raw organic sugar" or "raw organic flavored cane sugars" or other similar names. By blending raw organic liquid cane syrup with other plant extracts in liquid form, a crystallized sugar can be produced that combines both liquids. This crystallized sugar contains both the raw organic cane sugar and the extract of the fruit, vegetable, herb or spice. This crystallized sugar has an indefinite shelf life in dry granular form. Such plant-extract infused sugars are commercially available under the trade name "EssentialCane" from Flavorstorm Inc of Woodinville, Wash.

In some embodiments, unrefined cane sugar may be used without infusion of supplemental plant extracts.

Unrefined cane sugar contains AHA (alpha hydroxy acid), specifically, glycolic acid. Glycolic acid may provide antioxidant properties. When included in a skin treatment, glycolic acid may provide an age defying effect; glycolic acid may help eliminate blemishes; glycolic acid may hydrate skin and may help balance skin oils. The total anti-oxidant content of refined sugars is less than 0.01 mmol FRAP/100 grams. (FRAP means ferric-reducing ability of plasma). Total anti-oxidant content of unrefined sugars is approximately 0.1 mmol FRAP/100 grams, or higher. This represents an order of magnitude increase over refined sugars. Unrefined sugar provides a higher anti-oxidant content than refined sugar.

Step 160 provides for selection of plants or plant extracts based on the desired health benefit. TABLE 1 shows a list of plants and associated health benefits (for example, when used topically on the skin).

TABLE 1

PLANTS AND ASSOCIATED HEALTH BENEFITS

| | |
|---|---|
| LEMON | astringent; lightens sun & age spots; evens out skin tone; provides amino acids & antioxidants; brightens complexion |
| TANGERINE | astringent; lightens sun & age spots; evens out skin tone; helps reduce wrinkles |
| GINGER | astringent; lightens sun & age spots; evens out skin tone; antiseptic for killing bacteria that causes acne; improves circulation; helps fight cellulite |
| VANILLA | contains vanillin, a polyphenol with potential antioxident capability; prevents mutations and stops the growth of cancer cells; reduces inflammation; calming, promotes serotonin release |
| MINT | astringent; contains salicylic acid to reduce inflammation; helps loosen dead skin cells; helps prevent clogged pore, preventing pimples and clears skin |
| LIME | astringent; lightens sun & age spots; evens out skin tone; brightens complexion |
| COFFEE | reduces inflammation; evens out skin tone; reduces appearance of cellulite & varicose veins |
| COCOA | antioxidant; provides flavanoids; maintains collagen to fight sun damage |
| STRAWBERRY | contains salicylic acid; provides antioxidants; reduces wrinkles and blemishes |
| RASPBERRY | antioxidant; provides polyphenolic compounds (known for their anti-cancer properties & sun protection) |
| BLUEBERRY | helps strengthen blood vessels and reduce varicose veins; helps normalize skin oil levels |

These plants (and similar plants, such as, other herbs, spices, vegetables, etc.) may be extracted or liquified to combine with cane sugar extract (and thereby, forming crystallized cane sugar granules). This cane sugar has an indefinite shelf life, that is, it has a very long shelf life. At the time of this patent application, Applicant only has knowledge of use of flavored, (i.e. infused), unrefined, organic cane sugar as food.

Now, we turn to four examples of blends of these plant-extract infused unrefined cane sugar.

Example 1

Skin scrub to provide a general purpose cleansing, including a mild astringent and antiseptic, anti-oxidant and oil balance. This skin scrub combines dry granules of the following: 2 parts tangerine-infused unrefined sugar, 1 part ginger-infused unrefined sugar, 2 parts vanilla-infused unrefined sugar, 2 parts blueberry-infused unrefined sugar, and 1 part bamboo-leaf infused unrefined sea salt.

Blueberry, raspberry, orange, ginger, vanilla and raw organic cane sugar are selected because of their anti-oxidant content that improve skin health.

Orange, blueberry, ginger, raspberry and raw organic cane sugar are selected for their wrinkle reducing characteristics.

Orange and ginger are selected for their ability to lighten sun spots.

Orange, ginger, vanilla, blueberry, raspberry and raw organic cane selected for their anti-oxidant content known for fighting free radicals and helping fight cancer.

Example 2

Skin scrub to provide relief for sun damaged skin. This skin scrub combines the following: 1 part espresso-infused unrefined sugar, 3 parts vanilla-infused unrefined sugar, 3 parts cocoa-infused unrefined sugar, 2 parts blueberry-infused unrefined sugar, and 1 part bamboo-leaf infused sea salt. Sun burn may not be healed when the skin is damaged beyond a certain point. This skin scrub may provide support for growth of soft new skin.

The espresso, vanilla, cocoa and blueberry are selected for their anti-oxidant content, hydrating and wrinkle reducing capabilities. Blueberry also neutralizes and normalizes oil levels in skin, minimizing likelihood of sebum accumulation. As sun damage occurs, blood vessel and capillary walls thin, causing varicose or spider veins. The coffee and blueberry may be capable of strengthening capillaries and blood vessels just below the surface of the skin. This improves circulation and hydration, which also promote skin health. The cocoa and vanilla may also promote collagen growth which aids new skin growth.

Example 3

Skin scrub to provide relief from acne, acne-induced skin damage, and acne-induced scarring. This skin scrub combines the following: 2 parts lemon-infused unrefined sugar, 2 parts lime-infused unrefined sugar, 2 parts mint-infused unrefined sugar, 2 parts blueberry-infused unrefined sugar, 2 parts strawberry infused unrefined sugar, and 1 part bamboo-infused sea salt.

The lemon, lime and mint are selected for their astringent characteristics which help remove unwanted skin oils. The strawberry and mint contain salicylic acid which breaks down blackheads and whiteheads. Salicylic acid also may cause the skin to properly shed dead cells. This helps prevent pores from getting clogged up and being infected with bacteria. The vitamin A & C in blueberry also assists with promoting proper hydration. The blueberry also helps neutralize and normalize skin oils. All components help reduce blemishes and discoloration that occur with acne scarring.

Example 4

Skin scrub to promote new skin growth and free-radical anti-oxidants. This skin scrub combines dry granules of the following: 2 parts strawberry-infused unrefined sugar, 2 parts raspberry-infused unrefined sugar, 2 parts blueberry-infused unrefined sugar, 2 parts vanilla-infused unrefined sugar, and 1 part bamboo leaf infused sea salt.

Blueberries, strawberries and raspberries are selected for the anti-oxidant content, which is among the highest of all fresh fruit.

The partial list of anti-oxidants found in these three berries (and other berries) is listed in table 2. Antioxidants are substances that protect the body by neutralizing free radicals or unstable oxygen molecules, which can damage the cells and are a major source of disease and aging.

TABLE 2

SOME ANTI-OXIDANTS FOUND IN BLUEBERRIES, STRAWBERRIES AND RASPBERRIES

| | |
|---|---|
| ANTHOCYANINS | These color pigments in berries are antioxidants. Blue, purple, and red color pigments associat with a lower risk of certain cancers, urinary tract health, memory function, and healthy aging. |
| CATECHINS | Catechins are flavonols that support the antioxidant defense system. Catechins are found in caneberries, green tea, red raspberries, evergreen blackberries, etc. |
| DIETARY FIBER | Found only in plant foods. Fiber helps maintain a healthy GI tract, lowers blood cholesterol, reduces heart disease and may prevent certain types of cancers. |
| ELLAGIC ACID | A phenolic compound known to provide anti-carcinogen, anti-viral and anti-bacterial properties. Known to prevent cancer and reverse tumors. |
| GALLIC ACID | Antioxidant also found in black tea and red wine; Inhibits cell proliferation and cell death in prostate cancer cells. |

TABLE 2-continued

SOME ANTI-OXIDANTS FOUND IN BLUEBERRIES, STRAWBERRIES AND RASPBERRIES

| | |
|---|---|
| PHYTOCHEMICALS | Phytochemicals are naturally occurring antioxidants in plants that add flavor, color pigments and scent, and they are abundant in all types of fruits and vegetables, particularly berries. The pigments that give berries their rich red to blue, black and purple colors are a type of phytochemical that has been shown to have significant disease-fighting, cell-protecting antioxidant capacity. |
| QUERCETIN | A flavonol that works as both an anti-carcinogen, an antioxidant and protects against cancer and heart disease. |
| RUTIN | A bioflavonoid that promotes vascular health, helps to prevent cell proliferation associated with cancer and has anti-inflammatory and anti-allergenic properties. |
| SALICYLIC ACID | The salicylic acid found in Oregon caneberries may prove to have the same protective effect against heart disease as aspirin. Aspirin is a closely related compound know to pharmacists as salicylic acid acetate. The therapeutic successes of small daily doses of aspirin to inhibit athero-sclerosis suggest the possibility that salicylic acid consumed in foods may provide a similar benefit. A 100-gram serving (about ¾ cup) of red raspberries contains around 5 milligrams of salicylic acid. |
| VITAMIN C | A water soluble vitamin that functions as a powerful antioxidant. |

Oxygen Radical Absorbance Capacity (ORAC) measures antioxidant activity. It measures the degree and length of time it takes to inhibit the action of an oxidizing agent. Antioxidants inhibit oxidation which is known to have a damaging effect on tissues. Studies now suggest that consuming fruits and vegetables with a high ORAC value may slow the aging process in both body and brain. Antioxidants are shown to work better when combined; the presence of fiber and other plant compounds enhance the health benefit. For this reason, a nutraceutical source may be a more viable antioxidant option than that of a dietary supplement. Likewise, combinations of various types of infused sugar may work better when combined.

These examples show how specific plants or plant extracts may be selected to achieve the desired health benefits (such as those described in table 2) of the dry scrub. Step 170 describes combining the dry granules of the selected infused unrefined sugars together. The unrefined sugars may be of varying granular size. This may provide an additional benefit during exfoliation, similar to different size of grit on sandpaper.

Raw organic sugar may be any kind of unrefined sugar, such as, raw cane sugar. Infused sugar may be any kind of imbued sugar, such as, sugar imbued with plant extracts (or other plant parts). Particles of sugar or salt may be any form of dry granules, such as, particles, grains, etc.

Step 180 provides for infusing bamboo leaf extract into sea salt granules. Bamboo leaf extract provides silica. Silica may improve absorption of calcium, potassium and magnesium. Silica may provide an antioxidant function and a wrinkle reducing function. Silica extracted from plant parts may be any kind of silica, such as, naturally occurring silica extracted by solvent from plants. Sea salt infused with bamboo plant extract is commercially available under the tradename "Hawaii Kai Gourmet Green" from H.K. Enterprise Group, which is also known as Hawaii Kai Corporation.

Step 190 provides for adding dry granules of sea salt to the dry-granular mixture. Sea salt may provide an antiseptic function, detoxifying function, circulatory improvement function, and inflammation reducing function. Sea salt contains calcium, potassium & magnesium.

Sea salt may be any type of sea salt, such as, unrefined sea salt containing naturally occurring calcium, potassium and magnesium; sea salt imbued with plant extracts (or plant parts), etc.

In some embodiments, the silica may be infused in the sugar granules. In other embodiments, the plant parts/extracts may be infused in the sea salt granules. In yet other embodiments, both silica and plant parts/extract may be infused in either granules.

Finally, step 195 packages the dry-granule mixture in a storage container, which is suitable for packaging, shipping, storing or retailing the dry scrub.

Figure 2:
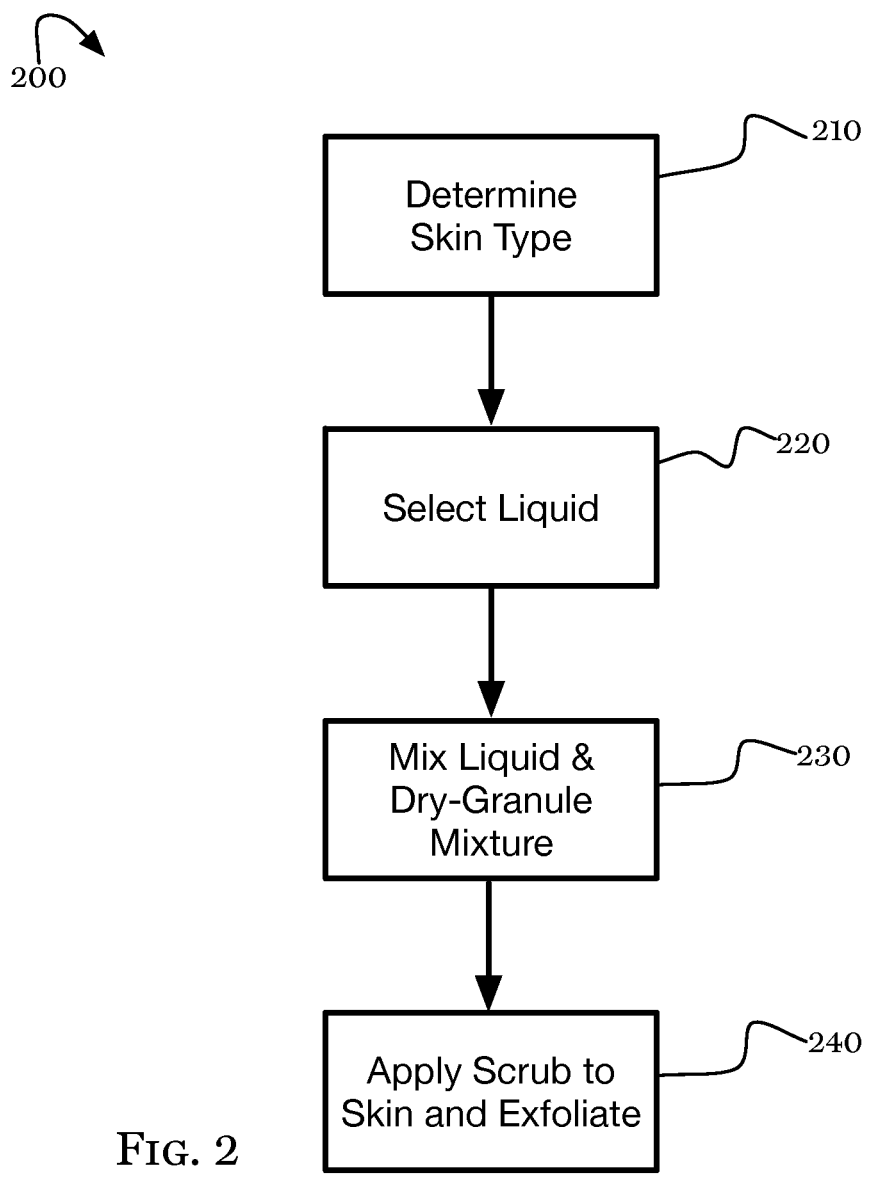
FIG. 2 shows a diagrammatic view that illustrates a method of treating the skin with a dry-granular mixture combined with a liquid to treat the skin.

FIG. 2 shows a diagrammatic view that illustrates method 200 of treating the skin with a dry particulate mixture combined with a liquid to clean or exfoliate. Step 210 determines skin type. For example, instructions may be provided with the storage container. The instructions may assist the person to determine the type of skin that they have: dry, oily, balanced, mixed, etc. Skin condition may periodically vary with diet, season, weather, environment, age, hormonal cycles, and other factors.

Step 220 selects a liquid carrier for the skin scrub. This step may provide further instructions to the user in selecting a liquid carrier appropriate for the skin type. TABLE 3 shows a list of liquid carriers and associated properties, including the skin type appropriate for the liquid carrier.

TABLE 3

EXAMPLE LIQUID CARRIERS AND ASSOCIATED PROPERTIES

| | |
|---|---|
| WATER | may be RO filtered, de-ionized, or other purified water; no additional AHA; refreshing feel compared to oil based scrubs during hot weather |
| VINEGAR | provides malic acid, which is another form of AHA; may be diluted with water |
| MILK/YOGURT | provides lactic acid, another form of AHA |
| OLIVE OIL | provides vitamin e and other hydrating and restorative components used to maintain healthy skin; may be desirable for dry skin |
| GRAPESEED OIL | is believed to help speed cellular repair and help even skin tone |
| KUKUI NUT OIL | quickly penetrates skin; provides linolenic fatty acids |
| ALMOND NUT OIL | provides vitamin e and vitamin b |
| WALNUT OIL | provides essential fatty acids to nourish and to hydrate skin; helps prevent UV damage |
| OTHER NUT OIL | varies, may not be suitable for people with allergies |

Another consideration may be the amount of glycolic acid (or AHA). Some liquid carriers may increase the level of AHA beyond what is desirable. Levels of AHA beyond 0.2 mmol/100 grams may begin to increase the skin's sensitivity to sun. So, honey and maple syrup (0.2-0.7 mmol/100 grams) and molasses (4.6-4.9 mmol/100 grams) may need to be used very occasionally or not at all to avoid complications with high AHA levels.

In some embodiments, a liquid carrier may be bundled with the dry-granular mixture for retail sale.

Step 230 provides instruction for mixing the liquid carrier with the dry-granular mixture. During this step the user will mix the dry-granular mixture with the liquid carrier. In one embodiment, a teaspoon of dry-granular mixture will be placed in the palm of the hand, and, liquid will be added to partially fill the palm. Mixing will partially dissolve the dry-granular mixture. Salt and sugar dissolve at different rates. Some combinations of dry-granular mixture and liquid carriers will result in a thickening of the liquid carrier. Step 240 provides that the mixture can then be applied to the skin to exfoliate and treat the skin.

Table 4 shows an example of directions to an end user:

TABLE 4

EXAMPLE DIRECTIONS

Directions: Shake container well before use. Place 1 level teaspoon of dry mix in palm of hand. Add ¾ teaspoon liquid (water, oil, milk or yogurt) to mix in palm and blend with finger tip. Apply to clean skin using circular motion to help exfoliate. Leave on skin for 5-7 minutes then rinse with cool water until skin is clean.

Although Applicants have described Applicants' preferred embodiments of this invention, it will be understood that the broadest scope of this invention includes modifications and implementations apparent to those skilled in the art after reading the above specification and the below claims. Such scope is limited only by the below claims as read in connection with the above specification. Further, many other advantages of Applicants' invention will be apparent to those skilled in the art from the above descriptions and the below claims.

What is claimed is:

1. A method to produce, store or ship a dry scrub for the skin of a person comprising the steps of:
   combining dry granules of sea salt and dry granules of unrefined sugar into a dry granule mixture, wherein the dry granules imbue silica extracted from bamboo plant;
   containing the dry granule mixture in a storage container; and
   providing instructions with the storage container to instruct how to select an appropriate kind and amount of liquid carrier to mix with a measured amount of dry granule mixture to partially dissolve the dry granule mixture in the liquid carrier to form a skin scrub;
   thereby allowing the person to scrub the skin.

2. The method of claim 1 wherein:
   the unrefined sugar includes glycolic acid sufficient to provide more than 0.01 mmol FRAP per 100 grams of unrefined sugar.

3. The method of claim 1 wherein:
   the sea salt includes calcium, potassium and magnesium.

4. The method of claim 1 wherein:
   the unrefined sugar includes glycolic acid sufficient to provide more than 0.01 mmol FRAP per 100 grams of unrefined sugar;
   wherein the sea salt includes calcium, potassium and magnesium.

5. The method of claim 4 wherein:
   the dry granules of unrefined sugar are imbued with plant extract other the cane extract.

6. The method of claim 4 wherein:
   the dry granules of unrefined sugar are imbued with ginger, vanilla, blueberry, and raspberry.

7. The method of claim 4 wherein:
   the dry granules of unrefined sugar are imbued with espresso bean, vanilla, cocoa, and blueberry.

8. The method of claim 4 wherein:
   the dry granules of unrefined sugar are imbued with lemon, lime, mint, blueberry, and strawberry.

9. The method of claim 4 wherein:
   the dry granules of unrefined sugar are imbued with strawberry, raspberry, blueberry, and vanilla.

10. The method of claim 4 wherein:
    the liquid carrier is water.

11. The method of claim 4 wherein:
    the liquid carrier is other than water.

12. A method to treat the skin of a person comprising the steps of:
    combining dry granules of sea salt and dry granules of unrefined sugar into a dry granule mixture, wherein the dry granules comprise silica extracted from bamboo;
    storing of the dry granule mixture in a storage container;
    mixing a liquid carrier, after the step of storing, with the dry granule mixture to partially dissolve the dry granule mixture in the liquid carrier to form a skin scrub; and
    applying the skin scrub to the skin of the person to treat the skin.

13. The method of claim 12 wherein:
    the unrefined sugar comprises glycolic acid sufficient to provide more than 0.01 mmol FRAP per 100 grams of unrefined sugar;
    wherein the sea salt includes calcium, potassium and magnesium.

14. The method of claim 13 wherein:
    the dry granules of unrefined sugar are imbued with tangerine, ginger, vanilla, blueberry, and raspberry.

15. The method of claim 13 wherein:
    the dry granules of unrefined sugar are imbued with espresso bean, vanilla, cocoa, and blueberry.

16. The method of claim 13 wherein:
    the dry granules of unrefined sugar are imbued with lemon, lime, mint, blueberry, and strawberry.

17. The method of claim 13 wherein:
    the dry granules of unrefined sugar are imbued with strawberry, raspberry, blueberry, and vanilla.

18. The method of claim 13 wherein:
    the liquid carrier is water.

19. The method of claim 13 wherein:
    the liquid carrier is other than water.

\* \* \* \* \*